(12) United States Patent
Koguchi et al.

(10) Patent No.: US 6,357,089 B1
(45) Date of Patent: Mar. 19, 2002

(54) CLIP FOR A SHEET ELECTRODE

(75) Inventors: Mikio Koguchi, Tokyo; Yoshikazu Kobayashi, Nara; Akiyasu Tsurushima, Kanagawa, all of (JP)

(73) Assignee: Sekisui Plastics Co., Ltd., Osaka (JP)

( * ) Notice: Subject to any disclaimer, the term of this patent is extended or adjusted under 35 U.S.C. 154(b) by 0 days.

(21) Appl. No.: 09/622,049

(22) PCT Filed: Feb. 23, 1999

(86) PCT No.: PCT/JP99/00812

§ 371 Date: Aug. 23, 2000

§ 102(e) Date: Aug. 23, 2000

(87) PCT Pub. No.: WO99/43257

PCT Pub. Date: Sep. 2, 1999

(30) Foreign Application Priority Data

Feb. 24, 1998 (JP) ............................................ 10-041606

(51) Int. Cl.[7] ........................ H01R 12/08; H01R 12/38; H01R 4/48
(52) U.S. Cl. .................... 24/536; 439/729; 439/909; 439/836; 439/499; 24/564; 24/330
(58) Field of Search ....................... 24/536, 564, 535, 24/327, 328, 330, 331; 439/370, 372, 499, 729, 835, 836, 909

(56) References Cited

U.S. PATENT DOCUMENTS

| | | | |
|---|---|---|---|
| 4,061,408 A | * 12/1977 | Bat et al. ..................... 439/729 |
| 4,555,155 A | 11/1985 | Drake | |
| 4,702,256 A | * 10/1987 | Robinson et al. ....... 439/729 X |
| 5,137,475 A | * 8/1992 | Olms ..................... 439/909 X |
| 5,454,739 A | * 10/1995 | Strand ......................... 439/729 |
| 5,944,562 A | * 8/1999 | Christensson ............... 439/729 |

FOREIGN PATENT DOCUMENTS

| | | |
|---|---|---|
| JP | 63-141277 | 6/1988 |
| JP | 64-39704 | 3/1989 |
| JP | 9-507769 | 8/1997 |

* cited by examiner

Primary Examiner—Robert J. Sandy
(74) Attorney, Agent, or Firm—Arent Fox Kintner Plotkin & Kahn, PLLC

(57) ABSTRACT

A clip for a sheet electrode, which is capable of easily and reliably pinching a sheet electrode, and capable of minimizing the number of parts, thus facilitating the assembling. This clip is constructed such that a movable plate (20) provided with slots (25) to be engaged with supporting axes (13) is engaged with a substrate (10) having the supporting axes (13), and a conductive leaf spring (30) which is bent in the near middle thereof is interposed between the substrate and movable plate so as to keep them in an opened state. After the insertion of a sheet electrode (50), the movable plate is pivoted against the force of the leaf spring so as to close and pinch the sheet electrode. When the movable plate is further shifted forward along the slots, the movable plate is fixingly engaged with the substrate, thereby maintaining the pinching of the sheet electrode.

11 Claims, 7 Drawing Sheets

CLIP FOR A SHEET ELECTRODE

FIELD OF THE INVENTION

The present invention relates to a clip for a sheet electrode useful for holding or pinching a sheet electrode which is designed to be adhered for example onto the surface of a living body (skin) for picking up bioelectric signals from the living body so as to deliver the bioelectric signals to an external device for the purpose of preparing an electrocardiogram or electromyogram.

BACKGROUND OF THE INVENTION

In the measurement of bioelectric signals as in the case of preparing an electrocardiogram, a sheet electrode comprising a sheet-like conductive terminal having a conductive polymer gel layer attached to one surface thereof is employed in such a manner that it is adhered through the polymer gel layer onto a chest or other portions of an examinee at first, and after the conductive terminal of the sheet electrode is pinched with a clip, bioelectric signals from the examinee are picked up and delivered via a conductive wire connected with the clip to a measuring apparatus for the evaluation.

As for the sheet electrode clip to be employed for the aforementioned purpose, several kinds of the clip have been disclosed for instance in Japanese Utility Model Unexamined Publication H6-74103. As shown in this utility model publication, so-called alligator clip which is usually employed is accompanied with a problem that since the conductive terminal of the sheet electrode is formed of a thin and slippery metal sheet, the clip is likely to be disengaged from the terminal while the terminal is pinched with the clip, thus leading to the generation of trouble in the examination. When the force of spring is increased in order to prevent the clip from being disengaged, the manipulability in the engagement and disengagement of the clip would be deteriorated, thus inviting another problem.

In the light of these problems, there is proposed in the above-mentioned utility model publication an electrode clip having a protrusion at a tip end thereof, which is designed to be inserted into a through-hole formed at an end portion of the conductive terminal of sheet electrode. This electrode clip is advantageous in that the sheet electrode can be reliably held by the clip as the through-hole to be engaged with the clip is formed at one end portion of the conductive terminal of sheet electrode. However, this electrode clip is still accompanied with the problems that it is troublesome in manufactural viewpoint to form a through hole in the sheet electrode, and at the same time, since the sheet electrode is accompanied with an adhesive layer, it is difficult to completely remove the tailings of the punched hole.

Additionally, the urging force of the spring of the clip is set so as to always close the tip end portion of the clip which pinches the conductive terminal of the sheet electrode. Therefore, it is required, at the occasion of employment, to maintain an opened state of the clip as opposed to the urging force of the spring, thereby enabling the conductive terminal portion to be inserted into the clip. In the light of such an operation, it is not necessarily easy to insert the protrusion formed on the clip into the through-hole formed at one end portion of the conductive terminal.

In any case, the conventional clips require not only a conductive member to be connected with a conductive wire but also a spring member to provide the clip with an urging force, thus necessitating a relatively large number of parts, and moreover, the assembling thereof is not easy. Further, since the conductive wire and the conductive member are integrally molded through an insert molding, it would be difficult to expect a high yield in the manufacture thereof and due to a high thermal stress in the manufacture thereof, it would be difficult to avoid the molded product from being easily broken.

The aforementioned utility model publication also discloses another embodiment of the electrode clip wherein a movable member is mounted on a substrate in such a way that it is enabled to slide in relative to and in parallel with the substrate, and the movable member is allowed, due to the elasticity thereof, to move forward beyond a protrusion formed on the substrate. Since a spring member for generating an urging force is not employed in this embodiment, the number of parts can be reduced. However, it would be difficult to allow the movable member to smoothly move along the surface of conductive terminal which is mounted on the substrate through an engagement between a through-hole formed in the conductive terminal and a protrusion formed on the substrate. Moreover, the conductive terminal may possibly be curled up due to the movement of the movable member.

BRIEF SUMMARY OF THE INVENTION

The present invention has been accomplished in view of the aforementioned problems, and therefore, an object of the present invention is to provide a clip for a sheet electrode, which is capable of easily pinching a sheet or film electrode (hereinafter referred to as a sheet electrode), capable of reliably pinching a sheet electrode without allowing the sheet electrode from being easily disengaged from the clip even if a conductive wire is pulled, capable of minimizing the number of parts so as to make the assembling thereof very simple, and capable of being stably used for a long period of time.

With a view to realize the aforementioned object, the present invention provides a clip for a sheet electrode, which comprises a substrate provided with supporting axes; a movable plate provided with slots which are adapted to engage with the supporting axes respectively; a leaf spring which is made of a conductive material, bent in the near middle thereof, i.e. U-shaped, interposed between the substrate and the movable plate, and connected with a conductive wire; wherein said leaf spring is always urged such that the fore-end portion thereof is kept in an open state; said movable plate is made pivotal in a direction to close the clip as opposed to the urging force of the leaf spring, thereby enabling a pair of distal ends of the leaf spring to contact with each other to pinch the sheet electrode therebetween; and said movable plate is enabled to shift forward along the slots while rendering the sheet electrode pinched between said pair of distal ends of the leaf spring and to rest while being kept engaged with the substrate. The clip can be also used for film electrode.

According to this clip for a sheet electrode, since the leaf spring is always urged such that the fore-end portion of the clip which is designed to hold a conductive terminal of sheet electrode is always kept in an open state, the sheet electrode can be easily introduced into the pinching portion of the clip. After the introduction of the sheet electrode into the pinching portion of the clip, the movable plate is pivoted in a downward direction as opposed to the urging force of the leaf spring, thereby enabling the conductive terminal of sheet electrode to be pinched and fixed from top and bottom by a pair of distal ends of the leaf spring which is made of a conductive material. While keeping this condition, the movable plate is then shifted forward so as to enable the movable plate to take a rested state mechanically. As a result, it is possible to prevent the sheet electrode from being disengaged even if an external force is inadvertently applied to the sheet electrode. When the movable plate is kept maintained in this state, the fore-end portion of the movable plate acts to cause the conductive terminal of the sheet electrode to press-contact with the distal end portion of the lower half of the leaf spring, thereby ensuring a reliable electric contact between the leaf spring and the conductive terminal of the sheet electrode.

When the sheet electrode is to be removed from the clip, the movable plate is pulled rearward from the rested position thereof. As a result, the engagement between the substrate and the movable plate can be easily released, and due to the force of the leaf spring, the movable plate is allowed to reliably return to the original opened state, thus allowing an easy removal of the sheet electrode.

According to this clip for a sheet electrode, since the leaf spring employed for giving an urging force is also functioned as a conductive member, it is no more required to provide additional conductive member for making a connection with the conductive wire. Further, since the leaf spring can be integrally formed with the conductive wire through fuse-bonding for instance, the resultant composite member being enabled to be assembled with the substrate, the number of parts can be minimized, thus facilitating the assembling thereof, and at the same time, it becomes possible to prevent the assembled body from being easily destroyed.

According to a preferable embodiment of the present invention, the movable plate is enabled, while the slot thereof is kept engaged with the supporting axes of the substrate, to pivot from the position where the fore-end portion of the movable plate is opened upward due to the urging force of the leaf spring to the position where the fore-end portion of the movable plate is further opened upward. Under this condition, the opened angle between the movable plate and the substrate can be enlarged, so that the assembling work such as the installation of the leaf spring onto the substrate can be facilitated.

According to a preferable embodiment of the present invention, the engagement between the movable plate and the substrate is effected through an engagement between a protrusion formed on the substrate and a cut-out groove formed in the movable plate. According to this mechanism of engagement, the manipulation to open and close the clip would become easy and at the same time, the engagement and disengagement of the sheet electrode can be reliably performed.

In a preferable embodiment of the present invention, both distal end portions of the leaf spring are provided with upright portions respectively, these upright portions being directed to face to each other. More preferably, at least one of these upright portions is provided at the tip end thereof with a large number of projected and recessed portions. When upright portions are formed in this manner, the engaged state of the conductive terminal portion of the sheet electrode can be further ensured, so that the sheet electrode can be reliably prevented from being inadvertently disengaged during the measurement operation using the sheet electrode.

According to another preferable embodiment of the present invention, the tip end portion of at least one of the halves of the leaf spring is provided with upright portions having different heights, and the tip end portion of the other of the halves of the leaf spring is provided with an upright portion which is designed to be inserted between said upright portions having different heights. When upright portions are formed in this manner, the conductive terminal portion of the sheet electrode can be pinched with said conductive terminal portion being bent accordingly. For example, the upright portion disposed on the movable plate side acts to push the conductive terminal portion of the sheet electrode into an interval between a pair of said upright portions disposed on the substrate side, thereby ensuring an excellent contact state, and at the same time, achieving a stable pinched and fixed state of said conductive terminal portion.

In another preferable embodiment of the present invention, said leaf spring is provided with a protruded portion for preventing the conductive terminal portion of the sheet electrode from excessively entering into the clip, thereby enabling the pinching position of the sheet electrode in the individual clip to be set to a fixed position, thus enabling to obtain a stable measurement value. By the way, this protruded portion may be formed perpendicular or be inclined rearward to the inserting direction of the sheet electrode in relative to the substrate under the condition where the sheet electrode is being pinched by the distal end portions of the leaf spring.

In another preferable embodiment of the present invention, said leaf spring is provided, at the portion facing the substrate, with an opening, and said substrate is provided with a projected portion which is designed to be engaged with the opening. When an opening and a projected portion are formed in this manner, the engagement of the leaf spring to the substrate can be further stabilized, so that the leaf spring can be reliably prevented from being inadvertently disengaged from the substrate.

In a further preferable embodiment of the present invention, a connecting portion between the leaf spring and the conductive wire is covered with a heat-shrinkable resin. When this connecting portion is covered with a heat-shrinkable resin, the stability of the connecting portion can be ensured, so that the connecting portion can be prevented from being inadvertently separated or from being exposed to a chemical.

By the way, the term "sheet electrode" employed in the present invention should be construed to include not only an electrode or an earth electrode, which is designed to be adhered onto the surface of a living body (skin) for picking up bioelectric signals from the living body for the purpose of preparing an electrocardiogram or electromyogram, but also an electrode which can be employed for introducing, through a skin, an external electric signal (of low frequency, for instance) into the interior of a living body or an electrode which can be employed in the general industrial purpose. These electrodes generally comprise, as an insulating substrate, a film of synthetic resin such as polyethylene terephthalate (PET), polyethylene, polypropylene, polystyrene, polyvinyl chloride, etc.; and an electric insulating material such as a synthetic paper, unwoven fabric, etc. On this insulating substrate, an electrode element coated with a silver paste, a silver/silver chloride paste, a carbon paste, etc., or a conductive material such as a metal foil is laminated to act as a conductive terminal (electrode element). On the portions of these electrodes which are to be adhered onto a living body, a conductive material layer comprising a natural polymer type conductive material such as cross-linked karaya gum, or comprising a conductive polymer gel such as sodium polyacrylate, polyacryl amide, etc. can be laminated.

DESCRIPTION OF THE PREFERRED EMBODIMENTS

Preferred one embodiment of the clip for a sheet electrode according to the present invention will be explained in details below with reference to the attached drawings.

Figure 1:
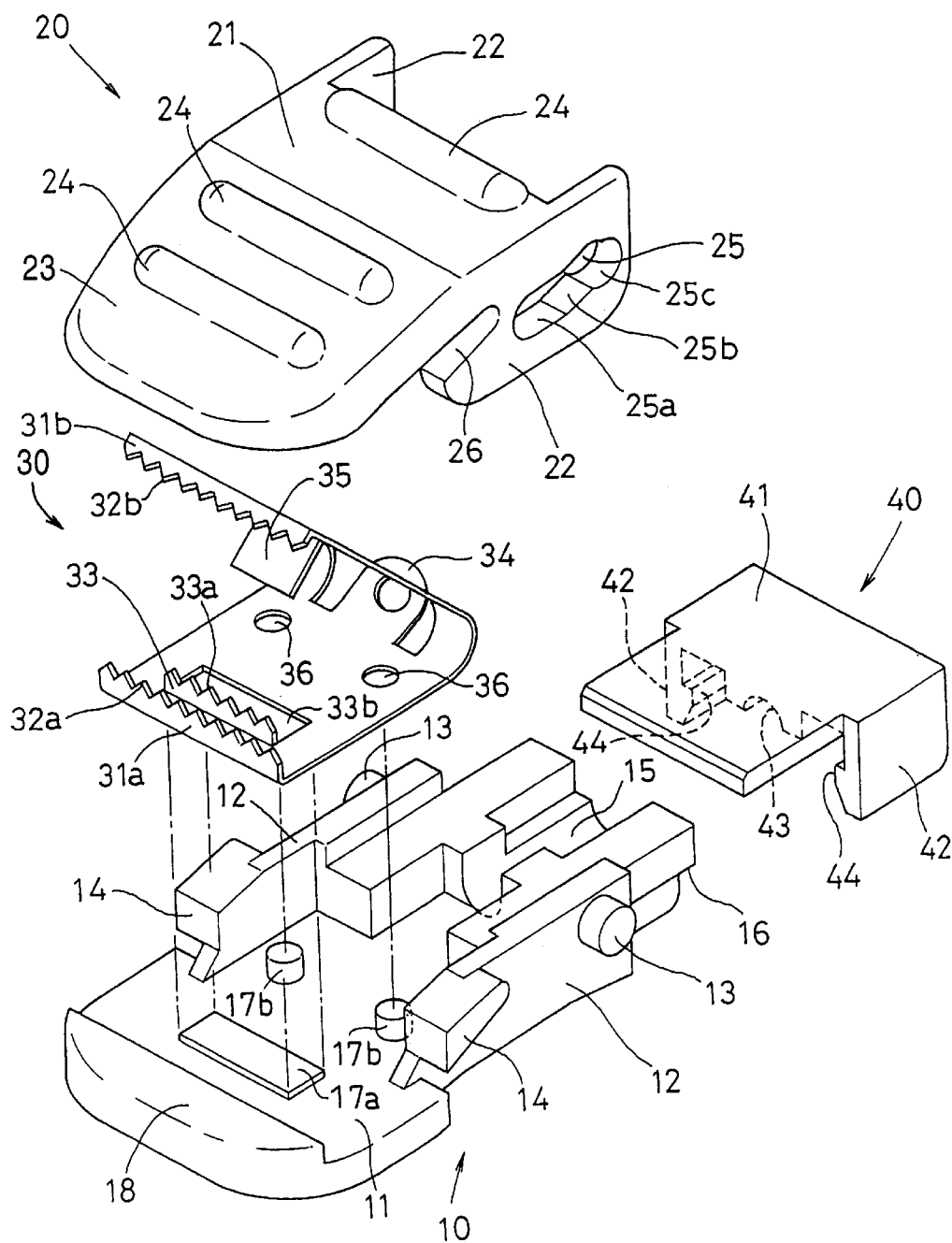
FIG. 1 is an exploded perspective view illustrating one embodiment of a clip for a sheet electrode according to the present invention.

Referring to FIG. 1, the substrate 10 is an integrated molded product made of a resin such as polyethylene terephthalate, polyamide and polyacetal, wherein a fore region of a bottom plate 11 is formed of a flat plate, and a pair of right and left side walls 12 are erected upward at a somewhat narrowed region located behind the aforementioned fore region. A pair of supporting axes 13 are externally and laterally extended (in the direction orthogonally intersecting with the longitudinal direction of the bottom plate 11) respectively from the rear upper portions of the side walls 12. Preferably, the distance between the tip ends of the supporting axes 13 should be the same as the traverse width of the fore flat plate region of the bottom plate 11. Further, a pair of projections 14 which are both laterally extended respectively from the fore upper portions of the side walls 12 and slightly inclined downward in the fore direction.

A passageway 15 having a cross-section is formed at the rear central region between the side walls 12, the passageway 15 extending in the longitudinal direction of the bottom plate 11. This passageway 15 is extended rearward farther than the side walls 12, and a step portion 16 is formed at each outer wall portion of the passageway 15. Further, a rectangular projection 17a is formed at the central portion of the fore flat plate region of the bottom plate 11. At the location behind the rectangular projection 17a, a pair of cylindrical projected portions 17b are projected, and the fore-end portion of the fore flat plate region is formed into a raised bed portion 18. A plural number of ribs 19 each extending transversely are formed on the bottom surface of the bottom plate 11 for the purpose of improving the manipulability thereof at the occasion of manipulating it with one's finger.

A movable plate 20 is an integrated molded product made of a resin which may be the same as that of the substrate 10, and has a width which is the same as that of the width of the fore flat plate region of the substrate 10. This movable plate 20 is constituted by an upper plate 21 and a pair of side walls 22 extending downward respectively from the right and left rear side portions of the upper plate 21. The width between the inner surfaces of the side walls 22 is approximately the same with the width between the outer surfaces of the side walls 12 of the substrate 10. The fore portion of the upper plate 21 is slightly inclined downward, thus forming an inclined surface 23. A plural number of ribs 24 are also formed on the upper surface and/or the inclined surface 23 of the upper plate 21 for the purpose of improving the manipulability thereof.

Figure 2A:
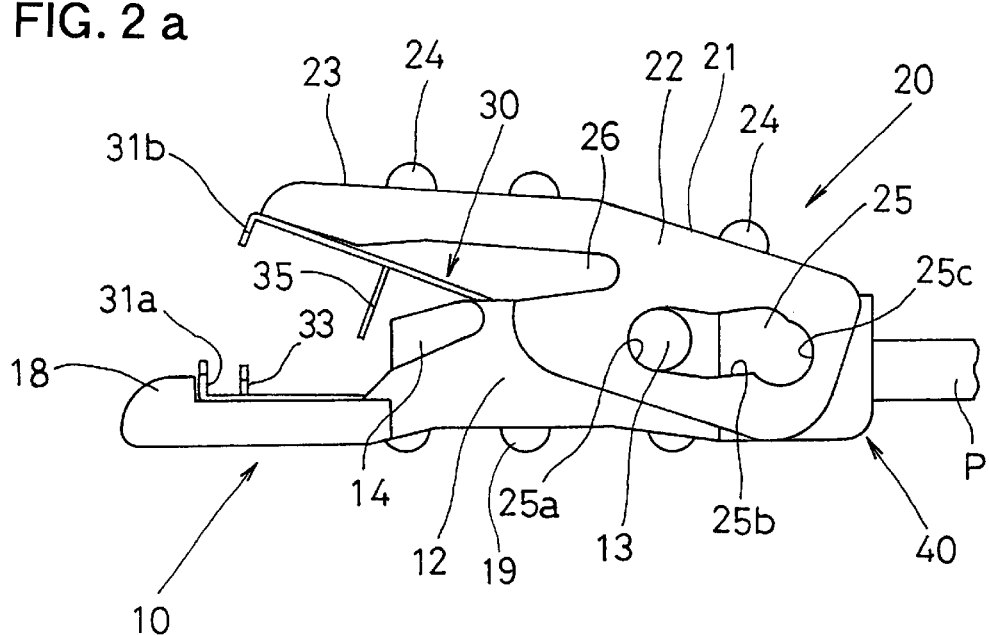
FIG. 2A is a side view illustrating a state where the fore-end of the clip shown in FIG. 1 is opened.
Figure 2B:
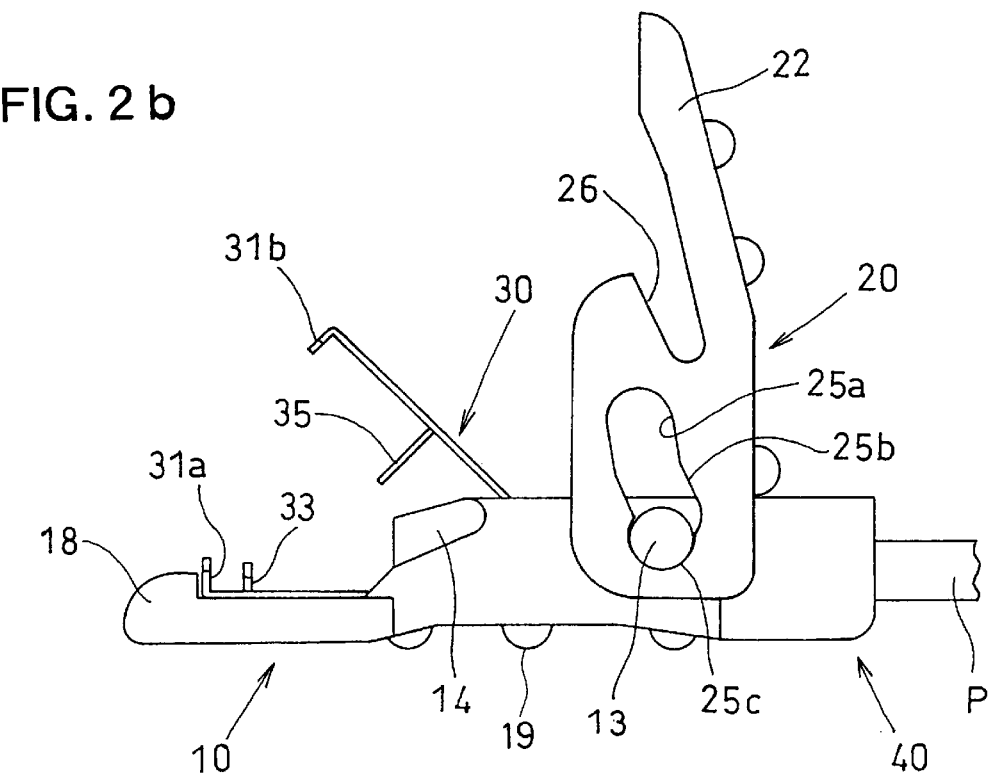
FIG. 2B is a side view illustrating a state where the fore-end of the clip is further opened.

A pair of slots 25 which are adapted to be engaged with the supporting axes 13 formed on the side walls 12 of the substrate 10 are formed in these right and left side walls 22. These slots 25 are inclined as a whole at the same angle as the inclined angle of the inclined surface 23. Preferably, as shown in the drawings, these slots 25 should be configured such that the fore zone 25a thereof is not inclined, the intermediate zone 25b thereof is inclined, and the rear zone 25c thereof is not inclined. Further, a pair of cut-out grooves 26 are formed at the fore-end portion of the right and left side walls 22, the angle of these cut-out grooves 26 being the same as the inclined angle of the inclined surface 23. These cut-out grooves 26 are adapted to be engaged with the projections 14 formed on the substrate 10. This movable plate 20 constructed as explained above is enabled, while these cut-out grooves 26 being engaged with the projections 14 formed on the substrate 10, to pivot from the posture thereof erected at an angle of about 90 degrees as shown in FIG. 2B down to the posture thereof inclined almost horizontally, thus contacting with the substrate 10.

Figure 5:
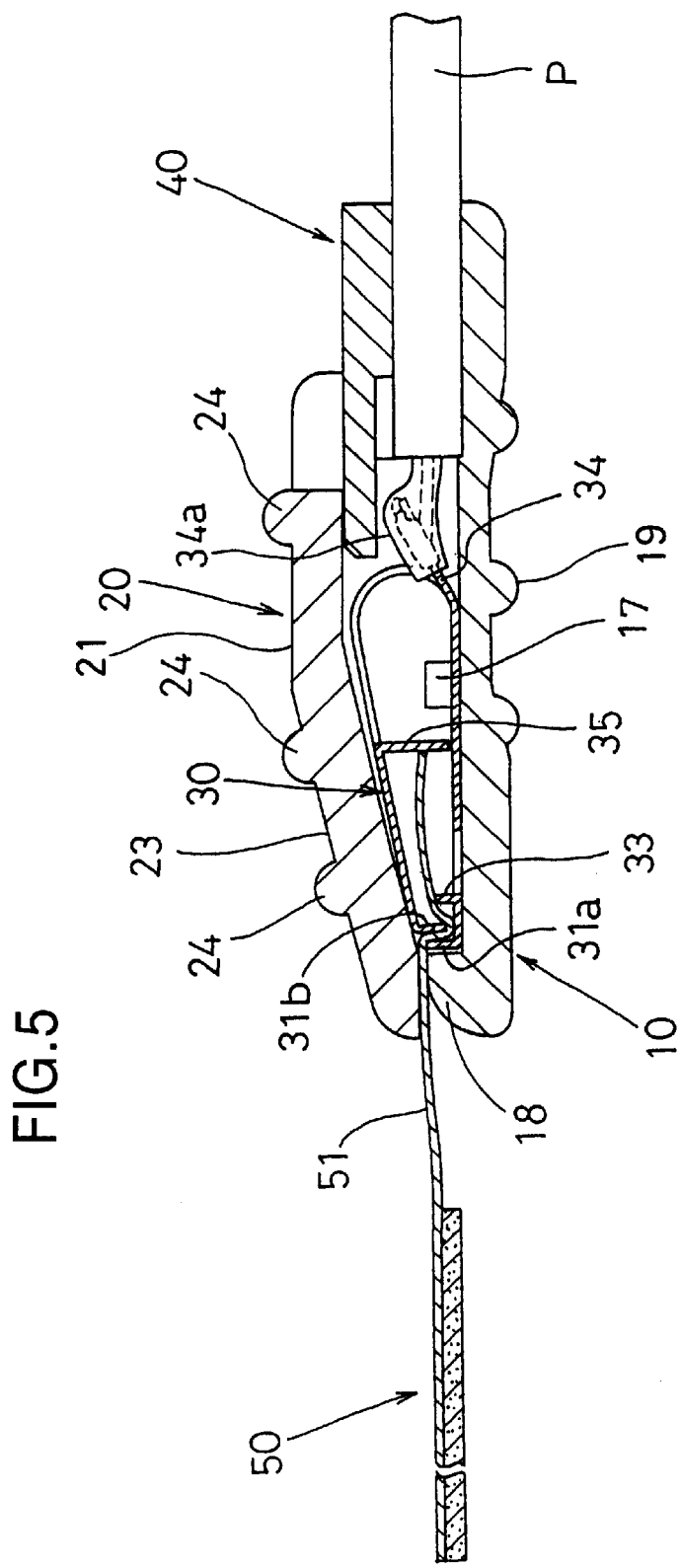
FIG. 5 is a cross-sectional view taken along the line V—V in FIG. 4.

A leaf spring 30 is bent in the near middle thereof, i.e. U-shaped, and is preferably formed of a single metal such as beryllium copper which is excellent in conductivity, anti-corrosion and fatigue resistance. However, this leaf spring 30 may be formed of a stainless steel such as SUS 301 with a gold plating. As for the size of the leaf spring 30, it may such that it can be entirely placed in the fore flat plate region of the bottom plate 11. The distal ends of the lower half and upper half of this leaf spring 30 are bent to form protrusions 31a and 31b respectively which face to each other. Further, according to this embodiment, a large number of projected and recessed portions 32a, 32b are formed on the distal ends of these protrusions 31a and 31b. Additionally, a second protrusion 33 is cut and raised on the inner side of the protrusion 31a formed on the lower half of the leaf spring 30. According to this embodiment, under the condition where the leaf spring 30 is closed as shown in FIG. 5, the protrusion 31b formed on the upper half of the leaf spring 30 is designed to be inserted into a space between the protrusion 31a and the second protrusion 33.

A portion in the vicinity of the curved portion of the leaf spring 30 is cut out so as to form therein a terminal 34 which is to be connected with a conductive wire P. Further, a protruded portion 35 directed downward is formed on the upper half of the leaf spring 30. The length of this protruded portion 35 should preferably be such that when the leaf spring 30 is closed as shown in FIG. 5, the protruded portion 35 is allowed to contact with the surface of the lower half of the leaf spring 30. The lower half of the leaf spring 30 is further provided with a pair of engaging holes 36 which are adapted to be engaged with the projections 17b formed on the bottom plate 11 of the substrate 10. A rectangular opening 33b formed as a result of the cutting to form the second protrusion 33 is designed to be engaged with the rectangular projected portion 17a formed at the central portion of the fore flat plate region of the bottom plate 11.

The reference number 40 represents a cover member to hold the conductive wire P, which is formed of an integral body made of a resin which may be the same as that of the substrate 10. This cover member 40 comprises an upper plate 41 which is designed to cover the passageway 15 from the top thereof, and a pair of right and left side walls 42. A passageway 43 for holding the conductive wire P in collaboration with the inner surface of the passageway 15 is formed at the rear portion of the bottom surface of the upper plate 41. Moreover, a pair of engaging step portions 44 are formed on the inner wall portions of the right and left side walls 42 so as to be engaged with the step portions 16 formed on the outer wall of the extended portion of the passageway 15.

In the assembling of the clip for a sheet electrode which is constructed as mentioned above, the terminal 34 of the leaf spring 30 is connected with the conductive wire P at first, and preferably, after a covering 34a made of a heat-shrinkable resin is attached to this connected portion, the projection 17a and the cylindrical projected portions 17b formed on the substrate 10 are respectively allowed to engage with the rectangular opening 33b and engaging holes 36 formed in the lower half of the leaf spring 30, thereby mounting the leaf spring 30 on the substrate 10. In this case, the length of the lower half of the leaf spring 30 is set in advance to such that, under the above condition, the protrusion 31a formed on the lower half of the leaf spring 30 can be disposed to nearly contact with the back surface of the raised bed portion 18 of substrate 10. Further, under this condition, the protrusion 31a and the bed portion 18 should be adjusted regarding their heights in such a manner that the upper end of the protrusion 31a is disposed higher than the bed portion 18.

Then, the conductive wire P is allowed to rest in the passageway 15, and the covering member 40 for holding the conductive wire is pushingly placed over the conductive wire P. Thereafter, the slots 25 of the movable plate 20 are allowed to engage with the supporting axes 13 of the substrate 10, thereby mounting the movable plate 20 in an upright state as shown in FIG. 2B, after which the movable plate 20 is pushed forward so as to make it pivot downward. As a result, the fore-end of the inclined surface 23 of the movable plate 20 is allowed to impinge upon the surface of upper half of the leaf spring 30. At this moment, due to the urging force of the leaf spring 30, the movable plate 20 is pushed up to take an obliquely raised posture. However, since the movement of the movable plate 20 is regulated by the configuration (locus) of the slots 25 and by the supporting axes 13, the postures of the movable plate 20 and the leaf spring 30 are balanced in a state where the supporting axes 13 are located at the fore zone 25a of the slot 25 as shown in FIG. 2A. Namely, the movable plate 20 is maintained in a posture where the fore pinching portion of the clip is opened.

When the sheet electrode 50 is to be pinched, the conductive terminal portion 51 of the sheet electrode 50 is introduced into the pinching portion which is kept in an opened state. Thereafter, the movable plate 20 is pushed downward as opposed to the urging force of the leaf spring 30. As a result, the movable plate 20 is caused to pivot about the supporting axes 13, and the protrusion 31b formed on a fore-end portion of the upper half of the leaf spring 30 is caused to be inserted into a space between the protrusion 31a and the second protrusion 33 formed on the lower half of the leaf spring 30. As a result, the conductive terminal portion 51 can be reliably pinched by these projected portions. By the way, when the conductive terminal portion 51 is introduced into the pinching portion of the clip, the fore-end of the conductive terminal portion 51 is impinged against the protruded portion 35, thereby making it possible to easily positioning the sheet electrode 50 at a predetermined position and to perform the measurement of large number of the clips under the same conditions.

Figure 3:
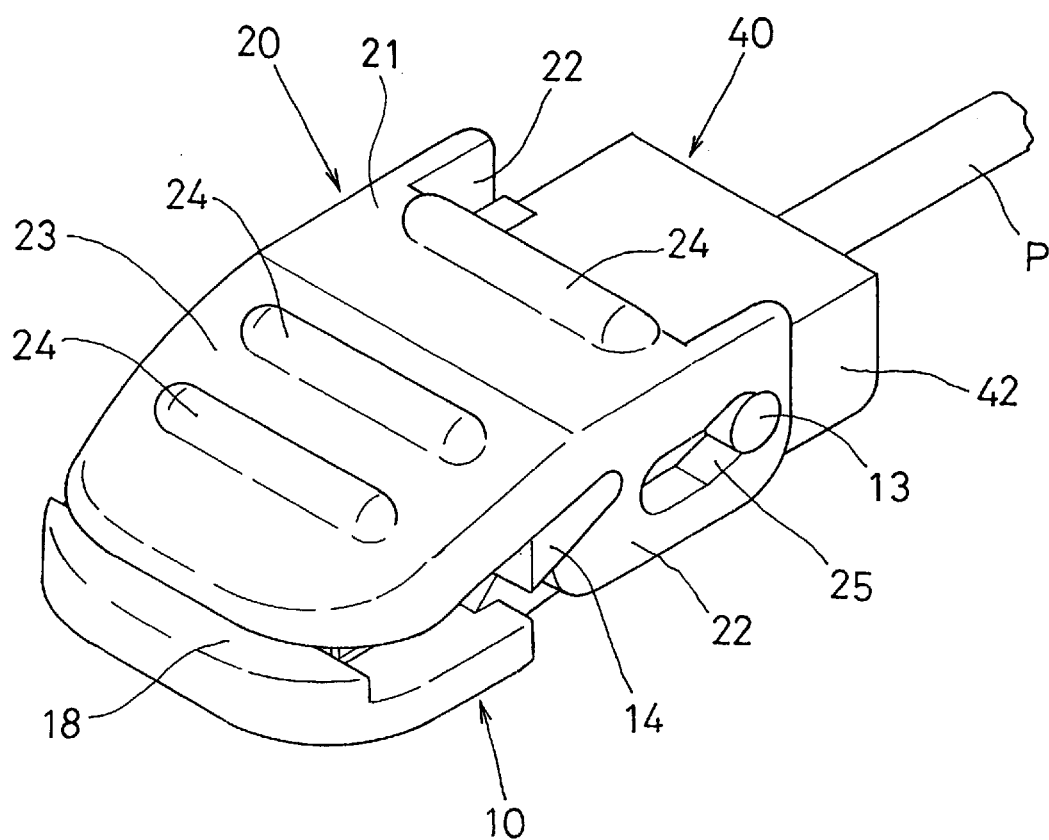
FIG. 3 is a perspective view illustrating a state where the fore-end of the clip is closed.
Figure 4:
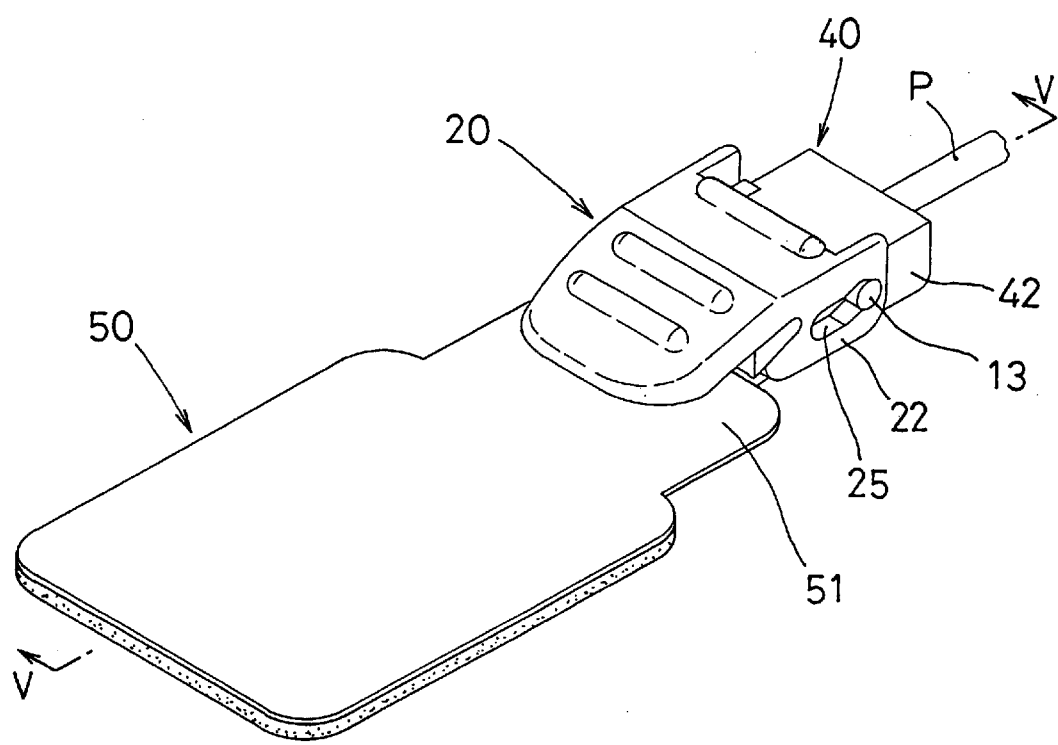
FIG. 4 is a perspective view illustrating a state where the fore-end of the clip is closed.

After the conductive terminal portion 51 is pinched in this manner, the movable plate 20 is pushed forward (in the leftward direction in the drawings) by means of one's finger tip. As a result, the movable plate 20 is allowed to advance along the locus (shape) of the slots 25 formed in the side walls 22 of the movable plate 20. Thereafter, the movement of the movable plate 20 is stopped at the rear end zone 25c. During this advancing movement of the movable plate 20, the cut-out grooves 26 are gradually brought to engage with the projections 14 formed on the side walls 12 of substrate 10, thus ultimately accomplishing a full engagement between the projections 14 and the cut-out grooves 26 as shown in FIG. 3. As a result, the movable plate 20 is brought into a finally engaged state with respect to the substrate 10, so that even if the movable plate 20 is released from one's finger, the movable plate 20 and the substrate 10 are kept in a state where the sheet electrode is kept pinched as shown in FIGS. 3, 4 and 5. Further, since the conductive terminal 51 is pressed by means of the bottom surface of the movable plate 20 onto the protrusion 31a formed on the lower half of the leaf spring, it is possible to obtain an excellently contacted state of the conductive terminal 51, and at the same time, the sheet electrode can be reliably prevented from being inadvertently disengaged from this engaged state. Preferably, as shown in FIG. 5, the size of the movable plate 20 is adjusted to such that the distal end portion thereof is just placed on the raised bed portion 18 of the substrate 10 under this conductive terminal-pinching condition.

In this embodiment, the slot 25 is inclined as a whole at an angle which is almost the same as the inclined angle of the inclined surface 23 of the movable plate 20. Therefore, during the process wherein the movable plate 20 is shifted from the fore zone 25a to the rear zone 25c of the slot, an downwardly pressing force is generated by the inclined surface 23 of the movable plate 20. Due to this downwardly pressing force, the pinching of the conductive terminal 51 between the protrusion 31b formed on the upper half of the leaf spring 30 and the protrusion 31a and second protrusion 33 formed on the lower half of the leaf spring can be increasingly enhanced, so that the sheet electrode can be reliably prevented from being inadvertently disengaged from this engaged state. When the inclined angle of the rear zone 25c of the slot 25 is set to an angle which is parallel with or somewhat leftwardly raised angle in relative to the surface of the substrate 10 under the condition where the sheet electrode is being pinched as shown in FIGS. 3, 4 and 5, the engagement of the movable plate 20 with the substrate 10 under the conductive terminal-pinching condition can be further stabilized.

When this pinched sheet electrode 50 is desired to be released from the clip, the movable plate 20 is pushed rearward (rightward direction in the drawings) by means of one's finger. As a result, the movable plate 20 is moved backward along the slot 25, and at the moment where the projections 14 are disengaged from the cut-out grooves 26, the movable plate 20 is forced to pivot upward by the effect of the urging force of the leaf spring 30, and hence, the movable plate 20 is brought back to the initial opened state. Under this condition, the sheet electrode 50 can be easily removed. Further, when the movable plate 20 is further pivoted upward to take the posture as shown in FIG. 2B, the cleaning or repair of the interior of the clip can be facilitated.

Figure 6:
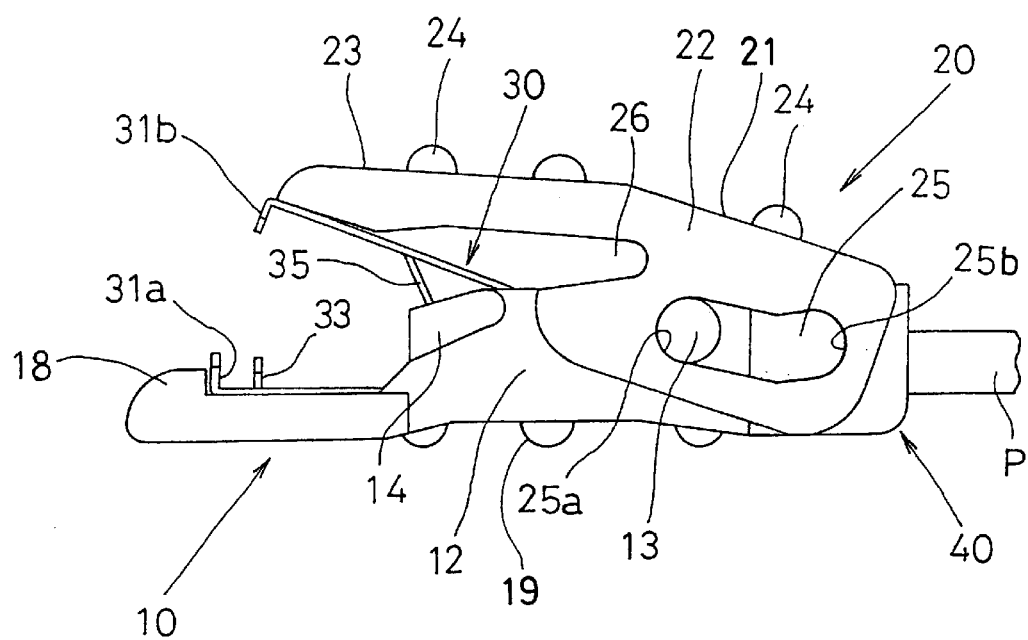
FIG. 6 is a side view illustrating another embodiment of a clip for a sheet electrode according to the present invention.
Figure 7:
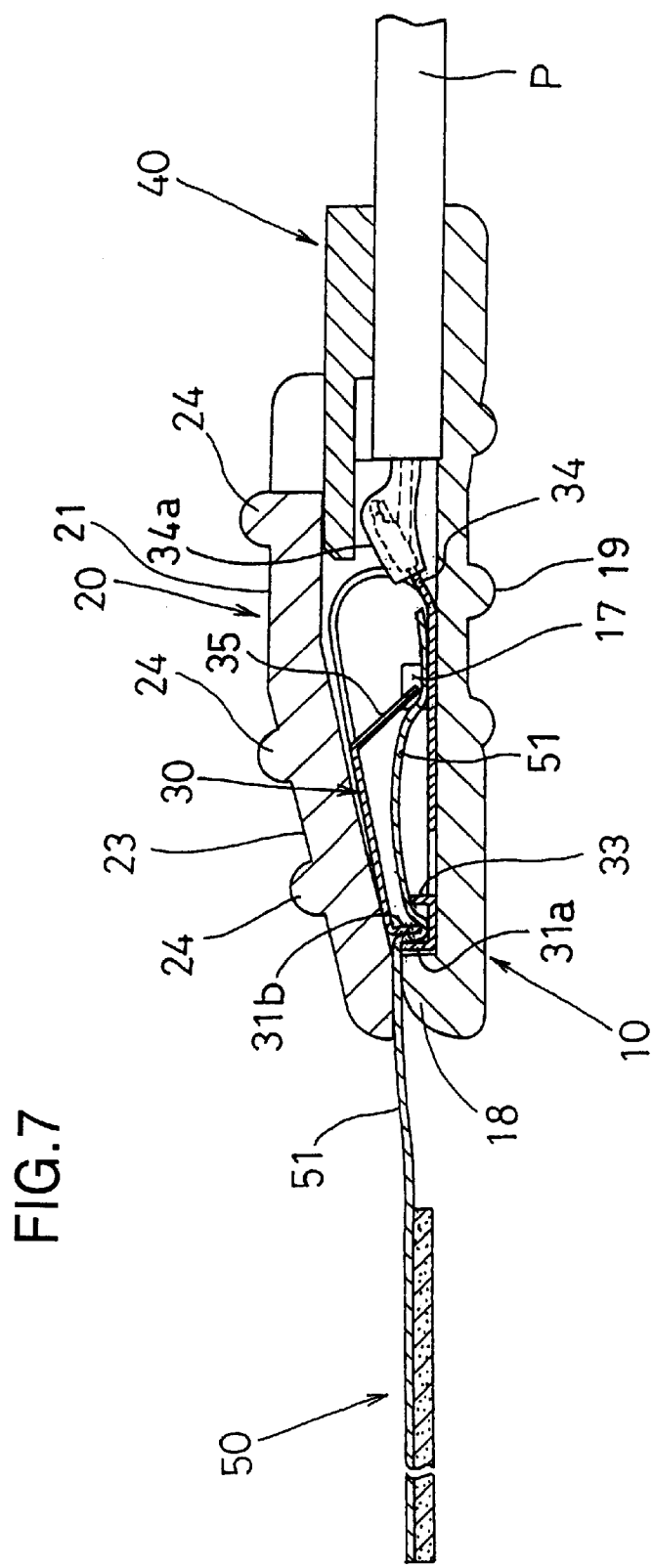
FIG. 7 is a cross-sectional view showing a state where a sheet electrode is pinched by the clip.

FIGS. 6 and 7 show another embodiment of the clip for a sheet electrode according to the present invention. This clip differs from that shown in FIGS. 1 to 5 in the respects that the protruded portion 35 formed on the leaf spring 30 is somewhat inclined in the rearward direction, and that the slots 25 formed in the right and left side walls 22 of the movable plate 20 are wide V-shaped as a whole in configuration, so that the rear zone 25c which is not inclined as shown in FIGS. 1 to 5 is absent from the slot 25. The constructions of other components are the same as those shown in FIGS. 1 to 5, so that the same parts are represented by the same reference numerals, thus omitting the explanation thereof.

Since the protruded portion 35 is somewhat inclined in the rearward direction, the introduction of the distal end of the conductive terminal 51 of the sheet electrode 50 can be further facilitated as the protruded portion 35 can be acted as a guide, and moreover, since the distal end of the protruded portion 35 can be acted to press the conductive terminal 51, the engagement of the sheet electrode 50 can be further stabilized. Additionally, since the slots 25 are wide V-shaped as a whole in configuration, the molding thereof can be further facilitated.

Although two kinds of projections 17a and 17b are formed on the substrate 10 for the purpose of stabilizing the attached posture of the leaf spring 30 in the embodiments shown in the drawings, one of them may be omitted.

According to this clip for a sheet electrode of the present invention, since the pinching portion of the clip is always kept in an open state, the operation of inserting, pinching and disengaging the conductive terminal of the sheet electrode can be greatly facilitated. Further, since the upper and lower members pinching the conductive terminal can be kept in an engaged state not through an elastic force but through mechanical means, it is possible to further ensure the pinching state of the conductive terminal and to prevent the conductive terminal from being inadvertently disengaged. Furthermore, since the leaf spring for keeping the open state of the pinching portion all the time is also enabled to function as a conductive member to be connected with a conductive wire, in addition to the function thereof as a pinching member, it is possible to minimize the number of parts and to facilitate the assembling thereof. Since the movable plate can be pivoted upward to take an upright posture, the cleaning or repair of the interior of the clip can be facilitated.

Further, since a conductive wire can be assembled in advance, through fuse-bonding for instance, with the leaf spring functioning as a conductive terminal-pinching member, and the resultant composite is assembled with the substrate, the possibility of generating defectives can be minimized as compared with the conventional structure where an electrode-contacting member is to be insert-molded together with a conductive wire. Therefore, the clip according to the present invention is more advantageous in an economical viewpoint. Furthermore, since the leaf spring and the conductive wire are subjected to a thermal stress in a reduced degree as compared with the conventional insert-molded product, it is possible to employ the clip in a stabilized condition for a long period of time.

What is claimed is:

1. A clip for a sheet electrode, which comprises;
    a substrate provided with supporting axes;
    a movable plate provided with slots which are adapted to engage with the supporting axes respectively;
    a leaf spring which is made of a conductive material, bent in the near middle thereof, i.e. U-shaped, interposed between the substrate and the movable plate, and connected with a conductive wire;
    wherein said leaf spring is always urged such that the fore-end portion thereof is kept in an open state; said movable plate is made pivotal in a direction to close the clip as opposed to the urging force of the leaf spring, thereby enabling a pair of distal ends of the leaf spring to contact with each other to pinch the sheet electrode therebetween; and said movable plate is enabled to shift forward along the slots while rendering the sheet electrode pinched between said pair of distal ends of the leaf spring and to rest while being kept engaged with the substrate.

2. The clip for a sheet electrode according to claim 1, wherein said movable plate is enabled, while the slot thereof is kept engaged with the supporting axes of the substrate, to pivot from the position where the fore-end portion of the movable plate is opened upward due to the urging force of the leaf spring to the position where the fore-end portion of the movable plate is further opened upward.

3. The clip for a sheet electrode according to claim 1 or 2, wherein the engagement between the movable plate and the substrate is effected through an engagement between a protrusion formed on the substrate and a cut-out groove formed in the movable plate.

4. The clip for a sheet electrode according to claim 1 or 2, wherein both distal end portions of the leaf spring are provided with upright portions respectively, these upright portions being directed to face to each other.

5. The clip for a sheet electrode according to claim 4, wherein at least one of these upright portions is provided at the tip end thereof with a large number of projected and/or recessed portions.

6. The clip for a sheet electrode according to claim 4, wherein the tip end portion of at least one of the halves of the leaf spring is provided with upright portions having different heights, and the tip end portion of the other of the halves of the leaf spring is provided with an upright portion which is designed to be inserted between said upright portions having different heights.

7. The clip for a sheet electrode according to claim 1 or 2, wherein said leaf spring is provided, at the portion facing the substrate, with an opening, and said substrate is provided with a projected portion which is designed to be engaged with the opening.

8. The clip for a sheet electrode according to claim 1 or 2, wherein a connecting portion between the leaf spring and the conductive wire is covered with a heat-shrinkable resin.

9. The clip for a sheet electrode according to claim 1 or 2, wherein said leaf spring is provided with a protruded portion for preventing the sheet electrode from excessively entering into the clip.

10. The clip for a sheet electrode according to claim 9, wherein said protruded portion is inclined rearward to the inserting direction of the sheet electrode.

11. The clip for a sheet electrode according to claim 1 or 2, wherein a plural number of ribs useful for pushing are formed on the bottom surface of the substrate and/or on the top surface of the movable plate.

* * * * *